United States Patent [19]
Alburger

[11] 3,949,601
[45] Apr. 13, 1976

[54] OPEN-LOOP WATER-WASHABLE INSPECTION PENETRANT PROCESS

[76] Inventor: James R. Alburger, 5007 Hillard Ave., La Canada, Calif. 91011

[22] Filed: Oct. 8, 1974

[21] Appl. No.: 513,105

Related U.S. Application Data

[63] Continuation-in-part of Ser. No. 432,752, Jan. 11, 1974.

[52] U.S. Cl. .................................................. 73/104
[51] Int. Cl.² ........................................ G01N 21/16
[58] Field of Search ......... 73/104; 23/230 R, 253 R, 23/230 C, 230 L; 134/10

[56] References Cited
UNITED STATES PATENTS

| | | | |
|---|---|---|---|
| 2,953,530 | 9/1960 | Switzer | 73/104 UX |
| 3,528,284 | 9/1970 | Skoglund | 73/104 |
| 3,764,265 | 10/1973 | Fijalkowski | 73/104 X |
| 3,814,695 | 6/1974 | Molina | 73/104 X |

*Primary Examiner*—Richard C. Queisser
*Assistant Examiner*—John P. Beauchamp

[57] ABSTRACT

A water-washable inspection penetrant process in which the penetrant is recovered for re-use and the used wash water remains sufficiently pure to be discharged into water disposal systems without causing excessive environmental pollution. A non-surfactant-type low-solubility penetrant which has been applied to test parts is wash-removed, leaving penetrant entrapments in crack defects. The thus-removed penetrant is separated from the wash water by allowing the mixture of water and removed penetrant to stand in a holding tank, whereupon the dispersed penetrant separates from the wash water and floats to the surface where it is collected for re-use. The relatively pure water is drawn from the bottom of the holding tank and is discharged into a water-disposal system.

3 Claims, 1 Drawing Figure

U.S. Patent    April 13, 1976        3,949,601
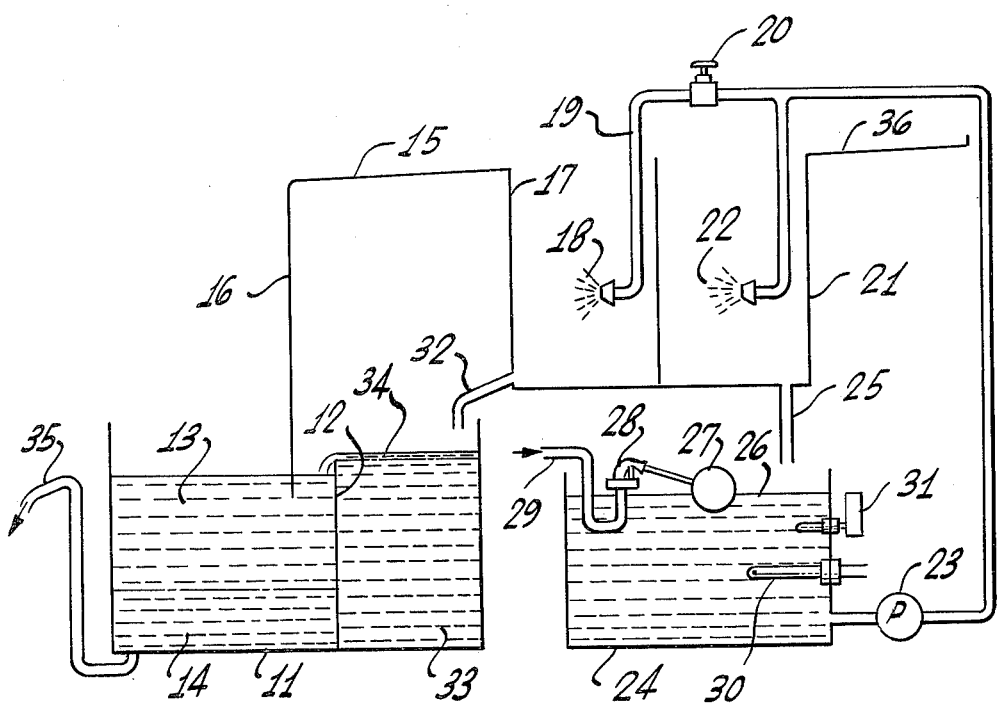

OPEN-LOOP WATER-WASHABLE INSPECTION PENETRANT PROCESS

This application is a continuation-in-part of my copending application Ser. No. 432,752, filed Jan. 11, 1974, for "A CLOSED-LOOP WATER-WASHABLE INSPECTION PENETRANT PROCESS."

RELATED PATENT APPLICATIONS

Application Ser. No. 482,465 — Filed June 24, 1974, for "ENHANCED STABILITY WATER-WASHABLE PENETRANT COMPOSITION AND PROCESS THEREFOR" now U.S. Pat. No. 3,896,664.

Application Ser. No. 431,236 — Filed Jan. 7, 1974, for "WATER-WASHABLE INSPECTION PENETRANT EMPLOYING MINERAL SOLVENT AND A FATTY ACID SOLUBILITY PROMOTER".

Application Ser. No. 513,084 — Filed Oct. 8, 1974, now U.S. Pat. No. 3,926,044 for "WATER-WASHABLE INSPECTION PENETRANT EMPLOYING TRIGLYCERIDES AND POLYGLYCERIDES OF FATTY ACIDS".

This invention relates to water-washable inspection penetrants and processes therefor. More particularly, the invention relates to methods and materials for recovery of the penetrant and the maintenance of pollution-free wash-water effluents.

In the past, it has been the practice to employ so-called "water-soluble" or "self-emulsifiable" compositions for use in the water-washable inspection penetrant process. The most commonly used water-washable penetrants are those of the "oil-phase" type, which comprise essentially an oily liquid containing a solution of indicator dye and sufficient detergent to render the oily liquid emulsifiable in water. Other types of penetrant compositions have been utilized in the past, for example water-soluble dyed liquids such as glycols or mixtures of glycols and water-soluble surfactants.

In any event, water-washable penetrants as employed in the past have all been characterized by an ability to dissolve in wash water or become emulsified upon contact with wash water. Test parts which are being inspected for the presence of surface crack defects are dipped in the water-washable penetrant and are allowed to drain. They are then washed with water to remove surface penetrant, leaving entrapments of penetrant in any crack defects which may be present. The entrapments of penetrant are revealed by the dissolved indicator dye, visible-color or fluorescent, as the case may be.

An alternate form of penetrant composition and usage is the so-called Post-Emulsifier Process, in which an oily water-insoluble dyed liquid penetrant is applied to test parts, following which a separate emulsifier is applied so as to render the oily penetrant emulsifieable in wash water. Emulsifiers for such usage are chemically equivalent to water-washable penetrants, except that they do not contain indicator dyes.

Water-washable penetrants (and comparable emulsifiers) are all characterized by the formation of relatively stable solutions or emulsions, and the dissolved or emulsified penetrant cannot be readily extracted or separated from the wash water. As a result, wash water which is employed for either the water-washable penetrant process or the Post-Emulsifier process contains considerable contaminants of emulsified or dissolved penetrant, and such contaminants have become an increasingly objectionable source of pollution in sewage systems or water disposal systems. In some cases, municipalities have legislated against disposal of any effluents containing contaminants of penetrants or emulsifiers.

Attempts have been made in the past to recover and re-use penetrant materials, and such attempts have been partially successful insofar as it has been found possible to recover a portion of the insoluble oily penetrant as used in the Post-Emulsifier process. Some penetrant may be stripped off of test surfaces by a pre-rinse under a high-pressure water spray, the thus-removed penetrant being collected by flotation and separation by skimming or re-capture over a drainage weir. However, Post-Emulsifier-type penetrant which is emulsified, the emulsifier itself, and of course water-washable penetrants, cannot be conveniently separated from the wash water.

Certain water purification methods have been devised, for example filtration systems utilizing activated carbon or other flocculating agents which serve to precipitate emulsified materials onto a solid clarifier. Methods of this kind have not proved to be entirely satisfactory, since there still exists the problem of disposal or re-cycling of the clarifier.

I have discovered that it is possible, through the use of certain types of water-washable penetrants, and through certain procedures of recovery, which will be described hereinafter, to separate used penetrant from the wash water so that it may be re-used. The wash water which remains after recovery of the penetrant contains a very low concentration of dissolved penetrant, which may be measured in parts-per-million, low enough to present a small degree of environmental pollution. Inasmuch as the process of the present invention serves to recover and re-cycle the penetrant and to discard the relatively pure wash water, I call this process an "Open-Loop" process, as contrasted with the "Closed-Loop" process of my copending application Ser. No. 432,752, of which this application is a continuation-in-part, and in which all process materials, including the wash water, are recovered and re-cycled.

The principal object of the invention, therefore, is to provide a water-washable inspection penetrant process in which the penetrant is recovered for re-use, and the wash water is maintained at a low level of contamination acceptable for discharge into water-disposal systems.

This and other objects of the invention will in part be obvious, and will in part become apparent from the following specification when read in conjunction with the drawing which is a diagram, in cross-section, showing a typical arrangement of apparatus as utilized in the process of the invention.

I have discovered that certain types of low-solubility water-washable inspection penetrants, which I have devised, and which contain no detergent, are adaptable to a mode of usage whereby used penetrant which is removed from the surfaces of test parts separates from the wash water and floats to the surface of the water where it can be collected and re-used. At the same time, the wash water dissolves an extremely small quantity of the penetrant, so that the contamination of the wash water does not exceed a few hundred parts per million. Penetrants which are suitable for use in the process of the invention are those which are characterized by a finite but relatively small solubility in water, and essentially no emulsifiability. At least three categories of these non-surfactant-type, low-solubility penetrants have been disclosed and claimed in my copending application Ser. Nos. 482,465, filed June 24, 1974, now U.S. Pat. No. 3,896,644 for "Enhanced Stability Water-Washable Penetrant Composition and Process Therefor", Ser. No. 431,236, filed Jan. 7, 1974, for "Water-Washable Inspection Penetrant Employing Mineral Solvent and a Fatty Acid Solubility Promoter", and Ser. No. 513,084, filed Oct. 8, 1974 now U.S. Pat. No. 3,926,044 for "Water-Washable Inspection Penetrant Employing Triglycerides and Polyglycerides of Fatty Acids".

I have found that any oil-compatible penetrant which is slightly soluble in water, but which is essentially "non-surfactant" in character, will function properly in the open-loop process of the invention. By "slightly soluble", it is meant that the penetrant is soluble in water to an extent which is less than a few percent concentration. I have found numerous suitable low-solubility penetrant compositions, some of which exhibit solubilities in water which are somewhat less than 0.01%. Examples of suitable penetrant compositions have been disclosed and claimed in my aforesaid copending application Ser. Nos. 482,465, 431,236, and 513,084.

In essence, the improved process of this invention involves, as a first step following application of penetrant to test parts, the removal of surface penetrant from the test parts by a spray-wash of water. As a second step in the process, the mixture of water containing droplets and globules of penetrant and partially dissolved penetrant is transferred to a holding-tank reservoir where it is allowed to stand and separate into layers, more-or-less pure penetrant floating on more-or-less pure water. Finally, the floating layer of penetrant is collected, either by means of a weir which skims off the penetrant, or the used wash water may be drawn out of the bottom of the holding-tank reservoir leaving the tank filled with recovered penetrant.

The penetrant compositions which may be utilized in the process of the invention are all characterized by an extremely low solubility in water, but not complete insolubility. Many of the preferred penetrant materials exhibit a "normal" characteristic of temperature-dependent solubility, whereby the solubility increases as the wash-water temperature increases. On the other hand, many of the preferred materials exhibit an inversion of solubility as a function of temperature, whereby the solubility decreases as the wash-water temperature increases. In either case, it is possible to adjust and control the rate at which penetrant is removed from the surfaces of test parts by adjusting the temperature of the wash water. Thus, it is possible to control the relative quantity of penetrant which is removed from a given crack entrapment by adjusting and controlling the washing time and/or wash-water temperature.

I have discovered that in order for a water-washable inspection penetrant to provide an acceptable flaw-detection performance, not only must the excess surface penetrant be removed from test parts, but some of the smaller entrapments of penetrant in micro-cracks must also be removed in order to avoid the formation of background indications which might obscure actual crack indications. In addition, I have discovered that each of the liquid solvent materials which I have disclosed as being suitable for use in the process of the invention has a characteristic rate of solution-depletion from surface micro-cracks. I have found that the rate of depletion of a given entrapment of penetrant can be defined in terms of the wash-water contact time, in seconds, required to deplete the brightness of the entrapment indication to half of its initial (undepleted) value. I call this time interval the "Indication Depletion Time Constant", and I have found that for practical purposes of handling test parts it is necessary that the indication depletion time constant must fall in the range of from a few seconds up to several hundred seconds, or possibly a thousand or more seconds, that is for typical background micro-crack indications. Since the rate of solution-depletion of entrapments of the various penetrant compositions of the invention depends on the particular liquid solvent which is utilized and on the temperature of the wash water, it turns out that certain of the solvent liquids may be preferred over others and certain wash-water temperature conditions may be preferred, depending on the desired depletion time constant and related performance characteristics.

The useful range of indication depletion time constant values may be very broad, from a few seconds up to a thousand seconds or more. Test parts may sometimes be processed by hand, and in such cases it may be desired that complete washing shall be accomplished within a few seconds. In other cases, such as in automated processing machines, the wash-water contact time may necessarily be very large due to the time required to manipulate the test parts and move them through the washing operation.

The so-called indication depletion time constant for a given penetrant material, as used in the process of the invention, depends mainly on the solubility of the liquid penetrant vehicle and the solubility of the indicator dye which is contained therein. The liquid vehicles which are disclosed in my above-mentioned copending application, Ser. Nos. 482,465, 431,236, and 513,084, all exhibit solubilities in water ranging from about 0.001% up to about 2% or 3%.

Non-surfactant-type penetrants which are soluble in water to concentrations greater than a few percent are not suitable for use in the process of the invention. Such penetrants are not only inefficient from the standpoint of retention of penetrant entrapments in crack defects, but they cause excessive contamination in the wash water. If the solubility of the solvent liquid in water is much less than about 0.001%, the indication depletion time constant becomes excessively large, and background indications, or even surface penetrant residues, are difficult to remove within a reasonable and practical washing time.

Preferred solvent liquids among those which are disclosed and claimed in my copending applications are those which exhibit solubilities in water ranging from about 0.01% up to about 0.5%. Liquids having greater solubilities, up to a practical limit of about 2% or 3%, may be utilized provided that ecological considerations will permit the resulting higher levels of contamination in effluent wash water. On the other hand, liquids having solubilities lower than the preferred minimum value of about 0.01% usually require excessively prolonged wash times.

I recognize that all chemical materials exhibit surface-active features, at least to some small degree. In my now-issued U.S. Pat. No. 3,751,970, for "Inspection Penetrant Process and Compositions for Aiding Removal of Excess Penetrant from Test Part Surfaces", I have disclosed numerous chemical substances which may exhibit detergency characteristics, either as surfactants or "synergists", even though these substances are not considered to have any surface-active properties, as surface-active materials are normally defined. In any event, for the purpose of the present invention, I define a non-surfactant-type penetrant composition as one which does not form an emulsion in water as normally occurs in the presence of conventional detergent materials.

It will be understood that the low-solubility penetrants which may be employed in the open-loop process of the invention may become dissolved in the wash water to a small degree, or they may become dispersed in the water by mechanical action of the spray-wash operation. I make no distinction between these two modes of mixing the penetrant with the wash water.

I have found that the rate of depletion of indications, and the degree to which background micro-crack indications are removed under given conditions of washing, depends in part on the nature of the indicator dye which is used, and its ability to become leached out of penetrant entrapments. Thus, in the case of certain solvent materials having extremely low water-solubility, I sometimes find that an acceptable effect of wash-removability of background indications can be obtained by virtue of the fact that the indicator dye is readily released from the solvent to become dispersed or dissolved in the wash water.

The process of the invention may be best understood by referring now to the FIGURE, which is a diagram in cross-section of a preferred arrangement of processing apparatus. A holding-tank reservoir 11 is divided into two parts separated by a partition 12 which acts as a weir to aid in skimming-separation of penetrant from wash water.

The left side of the holding tank reservoir is filled with a quantity of the low-solubility penetrant of the invention. This volume of penetrant 13 floats on top of a layer of used wash water 14. Parts being tested for the presence of crack defects are dipped into the penetrant in layer 13, or the penetrant is drawn from this layer and is applied to test surfaces by pressure spray, or electrostatic spray, or by other suitable means. The thus-treated test parts may then be allowed to stand and drain on a sloping drain-board 15. Penetrant drain-off is returned to the tank 11 by dripping down an extension 16 of the drain-board. This extension also serves as a baffle to minimize turbulence due to liquid which flows over the weir 12.

After the test parts are allowed to stand on the drain-board for a suitable penetrant dwell time, they are transferred to a first wash tank 17 in which they are suspended by means of suitable hangers or baskets. The parts are suspended in a wash-zone 18, which consists of an arrangement of spray nozzles fed by a system of piping 19. The flow of water into tank 17 and onto the test parts is controlled by a valve 20, which may be shut off when no parts are being processed in tank 17.

The test parts are left in the wash zone 18 only for a few seconds, long enough to flush off the surface penetrant. The parts are then transferred to tank 21 where they are suspended in a second wash zone 22. This second washing zone 22 consists of a spray of water which may be a mist or fog of water, sufficient to thoroughly wet the test surfaces and provide a good flushing action. The wash water supplied to wash zone 22 may run continuously, being supplied by a pump 23 from a wash-water reservoir tank 24. Water which drains from the test parts in wash zone 22 drains back into tank 24 through a drain pipe 25.

The water in tank 24 is maintained at a constant level 26 by means of a float mechanism 27 and a valve 28. Water is supplied to this reservoir from a hot water line through an entrance pipe 29. Either an external hot water heater may be used, or an immersion-type heater 30 may be utilized, the water temperature being controlled by means of a thermostat 31.

Wash water which is circulated through tank 21 picks up very little penetrant, since the only penetrant which can dissolve in this water is the minute amounts which are in micro-cracks on the test parts. Thus, the degree of penetrant contamination in the water at this stage cannot exceed a few parts per million.

When the test parts are first placed in wash zone 18, the bulk of the surface penetrant is removed by a mechanical scrubbing action of the wash water droplets. At this stage of the process, the penetrant cannot dissolve in the water to a concentration greater than the solubility which pertains at the wash-water temperature which is utilized. Preferred penetrant materials may have solubilities in the range of from about 10 to 200 parts per million at wash water temperatures in the range of from about 100° F. to 150° F.

If the flow of water in zone 18 is limited to the minimum amount required for removal of surface penetrant, the amount of dissolved penetrant may approach the saturation point (10 to 200 parts per million as indicated), but if a more-or-less continuous water flow is utilized, then the amount of dissolved penetrant may be much less, and may be only a few parts per million.

The flow of water from zone 18 carries droplets and globules of penetrant through a drain pipe 32, from which it drains back into the holding tank reservoir 11. The water-penetrant mixture remains in tank 11 long enough for the penetrant to float to the surface leaving relatively pure water at the bottom of the tank. Tank 11 is preferrably divided into two or more sections, as shown, separated by drainage weirs 12. This allows the retention of large volumes of water 33 in each section, permitting the penetrant to separate by flotation into a layer 34 before draining back into the main body of penetrant 13.

As water is used in wash zone 18, the overflow of clean water is discharged from a stand-pipe 35. This effluent water may be drained into another holding tank, if desired, where it can be allowed to stand for a longer time to insure that no entrainments of penetrant are carried out of the system. As long as the system is used properly, so that complete flotation-separation occurs, in tank 11, the only loss of penetrant which can occur is that which is carried out in entrapments in test parts and that which is dissolved or dispersed in the wash-water effluent from pipe 35.

After washing is completed, in wash zone 22, the test parts are allowed to stand on a sloping drain-board 36 where they drain and dry. Alternatively, the parts may be placed in an oven or in a stream of warm air for the purpose of drying. The parts may finally be inspected in accordance with conventional practice, by examination for flaw indications under black light where the indicator dye is fluorescent, or by examination under white light where the indicator dye is visible-color in character.

I do not limit the process of the invention to any specific arrangement of apparatus, since the various reservoirs, spray tanks, pipe lines, and other pertinent apparatus may be constructed and arranged in a wide variety of ways. In some cases, it is not even necessary to utilize tanks or containers to carry out the process. For example, where large aircraft wing spars or large engine parts are to be inspected, the steps of penetrant application, spray-washing, drying, development, and inspection, can all be carried out in a single large room having a concrete floor with a catch-basin or sump for collecting the used process materials. The used penetrant and wash water are pumped out of the sump and into a large holding tank where flotation-recovery of the penetrant takes place, and from which the relatively clean water overflows into a sewer or other disposal system.

It will be understood that techniques of spray-wash recovery of post-emulsifier-type penetrants have been employed in the past. In processes of this kind, test parts are treated with an oily water-insoluble penetrant. Then, for the purpose of recovery of most of this penetrant, the parts are spray-washed with water in a manner similar to the procedure which is carried out in wash-zone 18 of the FIGURE.

Since conventional water-insoluble post-emulsifier-type penetrants do not have any appreciable degree of water solubility, they do not dissolve in the wash water, or at least their effective depletion time constant values are so large that they are beyond the maximum useful range of about a thousand seconds, and well beyond the preferred limit of a few hundred seconds which I have indicated as being desirable for the process of the present invention. Hence, it has always been the practice, in the post-emulsifier process to transfer the penetrant-treated test parts into an emulsifier bath which acts to render the penetrant water-emulsifiable. After a suitable dwell time in the emulsifier, the parts are washed with water so as to remove the emulsifier and emulsified penetrant.

It will be understood that prior to my discovery of the feature of indication depletion it was not known that low-solubility solvent liquids of the types disclosed in my above-mentioned copending applications could be used as base vehicles for water-washable inspection penetrants. Accordingly, only two types of penetrant processes involving the use of wash water were available to penetrant users, and in both of these processes the penetrant and/or emulsifier become dispersed in the wash water and do not separate to leave relatively clean wash water such as is accomplished in the process of the present invention. In conventional processes of the water-washable type, the penetrant disperses in wash water in the form of an emulsion. Likewise, in the post-emulsifier process, whether or not a step of spray-wash penetrant recovery is utilized, a final washing step is employed in which the emulsifier and emulsified penetrant become dispersed in the wash water as an emulsion.

The emulsions which form in conventional penetrant processes cannot be separated from the wash water by simple flotation, and even if they are separated by filtration through activated carbon or by other means, they cannot be conveniently re-cycled and re-used in the penetrant process. It will be understood that the process of the present invention provides a simple and inexpensive method for the recovery and re-use of penetrant liquid and the minimization of environmental pollution due to contamination of wash-water effluents.

It will be understood that the temperature of the wash water as used in the process of the invention may have any temperature from room temperature, or the temperature of tap water, up to the boiling point of water. Improved performance in wash-removal of penetrant from test parts is obtainable by the utilization of wash water at elevated temperatures, therefore a preferred range of wash water temperatures is from about 100° F. up to the boiling point of water.

It will be seen from the foregoing specification that I have devised a new and novel process for the utilization and re-use of water-washable penetrant materials and the clarification of wash water in the inspection penetrant method. Although the invention has been described with reference to particular embodiments thereof, it will be understood that various changes may be made therein without departing from the spirit of the invention or the scope of the appended claims.

What is claimed is:

1. In a water-washable inspection penetrant process in which a water-removable dye liquid penetrant is applied to a test surface and excess surface penetrant is removed by washing said test surface with water, leaving entrapments of said penetrant in any crack defects which are present, the improvement which permits recovery and re-use of said penetrant and the clarification of said wash water to a low level of penetrant contamination acceptable for discharge into sewage systems, wherein said penetrant is a non-surfactant-type low-solubility water-washable composition, and wherein said penetrant is utilized in the following sequential steps: (1) apply said penetrant to test surfaces from a holding-tank reservoir containing said penetrant floating on a layer of wash water, (2) spray-wash said test surfaces with water under controlled conditions of wash-water temperature and wash time, (3) return the mixture of wash water and partly dissolved penetrant which drains from said test surfaces to said holding-tank reservoir, allowing it to separate by flotation into layers of re-usable penetrant and clarified wash water containing a relatively low concentration of dissolved penetrant, and (4) discharge said used wash water from said holding-tank reservoir while retaining said penetrant for re-use, said penetrant being soluble in water to a concentration within the range of from about 0.001% to about 3%.

2. In a water-washable inspection penetrant process in which a water-removable dyed liquid penetrant is applied to a test surface and excess surface penetrant is removed by washing said test surface with water, leaving entrapments of said penetrant in any crack defects which are present, the improvement which permits recovery and re-use of said penetrant and the clarification of said wash water to a low level of penetrant contamination acceptable for discharge into sewage systems, wherein said penetrant is a non-surfactant-type low-solubility water-washable composition, and wherein said penetrant is utilized in the following sequential steps: (1) apply said penetrant to test surfaces from a holding-tank reservoir containing said penetrant floating on a layer of used wash water, (2) spray-wash said test surfaces with water under controlled conditions of wash-water temperature and wash time, (3) return the mixture of wash water and partly dissolved penetrant which drains from said test surfaces to said holding-tank reservoir, allowing it to separate by flotation into layers of re-usable penetrant and clarified wash water containing a relatively low concentration of dissolved penetrant, and (4) discharge said used wash water from said holding-tank reservoir while retaining said penetrant for re-use, said penetrant being soluble in water to a preferred concentration within the range of from about 0.01% to about 0.5%.

3. A process in accordance with claim 1 in which said wash water is maintained at an elevated temperature above about 100° F. up to the boiling point of water.

* * * * *